United States Patent [19]

Le Fur et al.

[11] Patent Number: 5,256,649
[45] Date of Patent: Oct. 26, 1993

[54] COSMETIC COMPOSITION AGAINST AGING OF THE SKIN

[75] Inventors: Gérard Le Fur, Montmorency; Michel Sabadie, Bernay, both of France

[73] Assignee: Elf Sanofi, Paris, France

[21] Appl. No.: 887,604

[22] Filed: May 22, 1992

Related U.S. Application Data

[63] Continuation of Ser. No. 527,210, May 23, 1990, abandoned.

[30] Foreign Application Priority Data

May 23, 1989 [FR] France ............... 89 06747

[51] Int. Cl.$^5$ ............................................. A61K 31/70
[52] U.S. Cl. ........................................ 514/46; 514/556; 514/844
[58] Field of Search ................... 514/46, 556, 844

[56] References Cited

U.S. PATENT DOCUMENTS

| | | | |
|---|---|---|---|
| 3,819,480 | 6/1974 | Hochschild | 514/562 |
| 4,148,762 | 4/1979 | Koch et al. | 252/544 |
| 4,490,355 | 12/1984 | Desal | 424/70 |
| 4,497,825 | 2/1985 | Bade | 514/556 |
| 4,654,339 | 3/1987 | Hanefeld | 514/226 |
| 4,695,549 | 9/1987 | Grabitz | 435/267 |
| 4,702,913 | 10/1987 | Marty | 424/95 |
| 4,814,171 | 3/1989 | Marty | 424/95 |

FOREIGN PATENT DOCUMENTS

2609393  2/1988  France ................. 31/195

OTHER PUBLICATIONS

Biochemie, A. L. Lehninger, published by Verlag Chemie in 1975, pp. 483 and 484.
Merck Index 10th ed. p. 168 (1983).

*Primary Examiner*—Leonard Schenkman
*Attorney, Agent, or Firm*—Foley & Lardner

[57] ABSTRACT

The invention relates to a cosmetic composition comprising a mixture of
(a) betaine,
(b) ATP or an ATP generating system,
(c) a magnesium salt, and
(d) a potassium salt, in a cosmetically acceptable vehicle for topical administration and to a method for counteracting aging of the skin in a living human which utilizes the new composition.

16 Claims, No Drawings

COSMETIC COMPOSITION AGAINST AGING OF THE SKIN

This application is a continuation of application Ser. No. 07/527,210, filed May 23, 1990.

The present invention relates to a cosmetic composition for combatting aging of the skin which comprises an ademetionine generating system. The present invention also refers to a method of treating the skin to counteract aging by applying the new composition thereto.

Ademetionine is the International Non-proprietary Name for the inner salt of (S)-5'-[(3-amino-3-carboxypropyl)methylsulfonio]-5'-desoxyadenosine hydroxide of the formula:

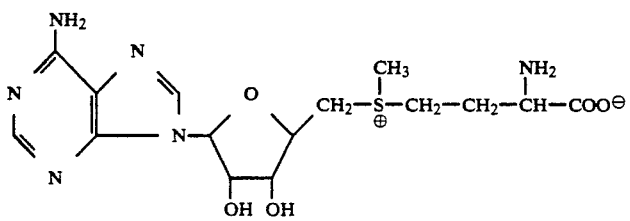

also indicated as S-adenosyl-L-methionine or, more simply, as SAMe.

Ademetionine is a physiological molecule, almost ubiquitously distributed within the organism tissues and fluids wherein it participates in important biological processes as a donor of methyl groups for a number of transmethylation reactions and as a precursor of physiological sulfur compounds such as glutathione, cysteine, taurine, and coenzyme A.

It is known that ademetionine levels are high in the infant and in the adolescent, they diminish in the adult and lower further in the pre-senile and senile age. It is also known that endogenous ademetionine forms at the cell level starting from methionine by the action of adenosyltransferase, of betaine as donor of methyl groups, and of adenosyltriphosphoric acid (ATP), in the presence of magnesium and potassium ions.

It has also been found (FR-A-2623396, published on May 26, 1989) that ademetionine has a skin anti-aging action and that it can be employed for cosmetic purposes directly on the skin.

The anti-aging effect of ademetionine is due to its biochemical properties. Transmethylation takes place on biological molecules, mainly on skin proteins, nucleic acids and phospholipids which are thereby biotransformed and enter the anabolic and catabolic cycles. This anabolic-catabolic activity at the epidermal cell level favours their regeneration while the action on methyltransferases, by increasing phospholipids methylation, make the cell membranes more fluid, thus slowing down the natural skin aging process. This membrane-fluidizing action has been demonstrated on human epidermal cells. The membrane microviscosity of human epidermal cells has been studied by the Shinitzky et al. method (J. Biol. Chem. 1974, 249, 2652-2657) using diphenylhexatriene as the fluorescent marker. The presence of ademetionine, at a molar concentration of from $10^{-6}$ to $10^{-4}$, reduces membrane viscosity by 10 to 25%.

However, for a cosmetic use, ademetionine has the disadvantage of being unstable and rather unsuitable to be handled in the cosmetic industry.

It has now been found, in in vitro tests, that betaine, also at very low concentrations, significantly affects ademetionine levels in human skin fibroblasts. It has also been found that it is possible to obtain the same effects observed with ademetionine by treating the skin with a mixture of betaine, ATP or an ATP generating system, a potassium salt and a magnesium salt, in a cosmetically acceptable vehicle, thus generating ademetionine in situ.

A first object of the present invention is therefore a cosmetic composition which comprises a mixture of:
(a) betaine,
(b) ATP or an ATP generating system,
(c) a magnesium salt, and
(d) a potassium salt, in a cosmetically acceptable vehicle for topical administration.

As used herein, the term "betaine" encompasses the compound of formula $(CH_3)_3N^+CH_2-COO^-$ as well as the corresponding addition salts with dermocompatible acids and the hydrated forms thereof.

The term "ATP generating system" or "ATP-GS" refers to any biological extract which is capable of increasing the respiratory cellular activity within the mithocondria, thus accelerating the cellular metabolism and hence the transformation of the products of the glycolysis and of the Krebs cycle into ATP. By increasing the respiratory cellular activity in the last step of the respiratory chain, ATP is generated immediately and directly via biochemical transformation of glucose in ATP, and then via the intermediate pyruvic acid which in its turn produces ATP (Lehninger-Principes biochimiques-Flammarion Medicine Science Ed., 1985, 497-498).

Among said biological extracts, those derived from eucaryotic cells, in particular from yeasts, and obtained by conventional extraction and purification processes which maintain the biochemical components of the cells, mainly amino acids, peptides and enzymes, almost intact, are preferred. These yeast extracts are known in the literature and are also commercially available, e.g. under the trade name VITACELL LS 1917 (manufactured by the French company Laboratories Sérobiologiques S.A.).

Also preferred are those biological extracts obtained from bovine spleen, well known in literature and commercially available, e.g. under the trade marks REVITALINE (manufactured by the Swiss company PENTAPHARM) and OXYDERMINE (manufactured by the French company SEDERMA). Such extracts are also obtained by conventional extraction and purification processes which maintain the biochemical components of the cells almost intact.

As far as the magnesium salt as well as the potassium salt are concerned, any organic or inorganic salt may suitably be employed provided it is dermocompatible.

Gluconates, pyroglutamates and chlorides are however the preferred anions.

British patent application GB-A-2,151,924 describes a cosmetic or dermatological composition for skin care which comprises, as essential components, a plant extract from *Oenothera biennis* and a spleen extract. While Oenothera oil is employed to create a barrier on the epidermis which controls the loss of water from the skin, the spleen extract is employed to activate the cellular respiratory activity, a well-known effect also referred to above. French patent application FR-A-2,608,393 claims pharmaceutical or cosmetic compositions, or compositions useful as bases for the preparation of pharmaceutical or cosmetic compositions which comprise a nitrogen containing compound such as an amino acid, an oligo- or poly-peptide, a protein or a derivative thereof, including also betaine. According to the teachings of said French patent application, which however does not describe compositions such as those defined in the present application, said preparations present-depending on the particular formulation-different activities: hydrating, nourishing, regenerating, protecting and stimulating the growth of epidermal and dermal cells or piliferous bulbs.

The components of the cosmetic preparations of the present invention may suitably be employed therein in the following proportions (the percentages are by weight):

| (a) betaine | from 0.001 to 1% |
|---|---|
| (b) ATP (or ATP-GS) | from 0.045 to 4.5% |
| (c) Mg$^{++}$ | from 10 ppb to 0.3% |
| (d) K$^+$ | from 0.0001 to 0.6% |

Preferably, said components are employed in the following proportions (the percentages are by weight):

| (a) betaine | from 0.03 to 0.3% |
|---|---|
| (b) ATP (or ATP-GS) | from 0.15 to 1.5% |
| (c) Mg$^{++}$ | from 15 ppb to 0.1% |
| (d) K$^+$ | from 0.001 to 0.2% |

Preferred cosmetic preparations according to the present invention comprise:

| (a) betaine | from 0.05 to 0.25% |
|---|---|
| (b) ATP-GS (such as yeast extracts such as e.g. VITACELL LS 1917 or bovine spleen extracts such as REVITALINE or OXY-DERMINE) | from 0.25 to 1% |
| (c) Mg$^{++}$ | from 20 ppb to 0.06% |
| (d) K$^+$ | from 0.002 to 0.1% |

For the preparation of the cosmetic compositions according to the present invention, the components are mixed with cosmetic excipients in order to prepare creams, lotions, emulsions or solutions.

In particular, the active components are admixed with the excipients conventionally employed in the cosmetic field such as for example, fats of animal or vegetal origin, vegetable oil, fatty acids, alcohols, polyalkylene glycols, waxes, petroleum jellies and polyesters, which can be used in association with water and jelling agents provided they are compatible therewith.

Other ingredients compatible with the active components, such as preservatives, e.g. 4-hydroxybenzoic acid esters, antioxidants, e.g. butylhydroxytoluene or vitamin E derivatives, or fragrances, can be added to these preparations. Fatty acids employed as adjuvants in the cosmetic compositions of the present invention may be saturated or unsaturated, may contain from 10 to 22 carbon atoms, be unsubstituted or hydroxy-substituted and in the form of the free acids or of the alkaline salts thereof.

The cosmetic compositions according to the present invention can be in the form of a cream wherein the active components are associated with the excipients which are commonly used in cosmetology and which are compatible therewith, such as lanolin or its derivatives.

The cosmetic compositions according to the present invention can also be in the form of a gel in a suitable excipient such as a cellulose ester, an acrylic polymer, a fatty acid ester, e.g. octyl palmitate or stearate, or other gelling agents.

According to another embodiment of the present invention, the above active principles are—at least in part—incorporated into phospholipid vectors, in the form of lamellar phases, spherical vesicles or hollow cylinders of phospholipid layers alternated with aqueous layers, generally designated as "liposomes". The selection of the phospholipids to be used in the preparation of the liposomes as well as the methods for the preparation and utilisation thereof in the liposomal compositions according to the present invention can readily be carried out by following the literature teachings (see for instance "Liposomes"-M. Ostro Ed., Marcel Decker, New York, 1983).

The cosmetic compositions of the present invention can also be in the form of a lotion, a solution or a microemulsion wherein the active components are dissolved or microdispersed. The cosmetic compositions according to the invention can therefore be in the form of a microdispersion of the components in a liquid containing water, oil and one or more surfactants. These dispersions have the same properties as microemulsions and the same appearance as true solutions. They can be prepared immediately before use. These microemulsions possess a good stability and can be stored for the time necessary for their use, at temperatures from 0° C. to 60° C. without sedimentation of the constituents or irreversible phase separation. The surfactants which can suitably be employed in these compositions are selected from those surface-active agents which can be used in cosmetology. As non-limiting examples there may be cited: sorbitol esters and their polyethoxylated derivatives, polyethoxylated castor oils (hydrogenated or non-hydrogenated), ethylene oxide/propylene oxide block polymers, polyethoxylated fatty alcohols and sterols, sodium laurylsulfate, sodium dioctylsulfosuccinate, egg or soya lecithins, and polyethoxylated silicon oils.

The effect of betaine on SAMe formation has been evaluated by the results obtained with betaine increasing concentrations in cultures of human skin fibroblasts. More particularly human skin fibroblasts (ATCC No. CRL 1513-2.10$^4$ cells/ml) have been cultured for 6 days in Dulbecco's Modified Eagle Medium (DMEM-250 ml containers) containing 20% of foetal calf serum, in the presence of increasing concentrations (from 10$^{-5}$M to 5.10$^{-4}$M)) of betaine. Then, the cells were taken off by treatment with trypsine (0.05%) and EDTA (0.02%) and centrifuged. The supernatant was separated, precipitated by the addition of trichloroacetic acid (0.2N, v/v) and centrifuged again. The supernatant was then recovered and lyophilized. The lyophilized material was taking up in water and analyzed by HPLC (column: Nucleosyl C8; Eluent: Solvent A (Sodium acetate 8.2 g, Sodium octylsulfonate 200 mg, Citric acid 4.2 g, EDTA 50 mg and water q.s. to 1 l) 95% and Solvent B (Methanol) 5%) using an U.V. detector at 260 nm. The amount of SAMe has been determined in comparison with a calibration curve prepared under the same experimental conditions.

| Betaine concentration ($10^{-5}$M) | SAMe concentration (nMoles/$10^7$ cells) |
| --- | --- |
| 0 | 0.54 |
| 1 | 0.62 |
| 5 | 0.94 |
| 10 | 1.72 |
| 50 | 1.90 |

By using the cosmetic compositions according to the present invention, which contain, in addition to betaine, ATP or an ATP generating system, a magnesium salt, and a potassium salt, after 30 days of regular application, a notable improvement in the appearance of the skin and a slowing down of wrinkle formation is achieved.

The cosmetic compositions of the present invention are therefore particularly suitable for:
slowing down aging by maintaining an optimum fluidity of the skin cell membranes, a high membrane fluidity favouring internal intercellular exchanges and hence the optimum metabolism;
improving the conditions of skins prematurely aged by the action of exogenous factors, via the above process.

Furthermore the cosmetic compositions according to the present invention are very well tolerated; they have no phototoxicity and their application to the skin for prolonged periods of time does not give rise to any systemic effect.

Another object of the present invention is therefore a method of treating the skin of a living human to counteract aging which method comprises applying to the skin a cosmetic preparation comprising an effective amount of a mixture of
  (a) betaine,
  (b) ATP or an ATP generating system,
  (c) a magnesium salt, and
  (d) a potassium salt,
in a cosmetically acceptable vehicle for topical administration.

The following examples are merely illustrative of the scope of the present invention and are not intended as a limitation to the scope thereof.

For the sake of simplification, certain constituents of the compositions have been indicated by their tradenames or abbreviations whose meanings are reported hereinbelow.

| | |
| --- | --- |
| VITACELL LS1917 | yeast extract manufactured by Laboratoires Serobiologiques S.A. |
| REVITALINE | bovine spleen extract marketed by Pentapharm |
| OXYDERMINE | bovine spleen extract marketed by Sederma |
| SOLUTOL HS 15 | polyethylene glycol 600 12-hydroxy stearate, marketed by BASF |
| CETIOL HE | polyethylene glycol-7 glyceryl cocoate marketed by Henkel |
| LABRAFAC HYDROPHYLE | polyethoxylated triglycerides containing 7–8 carbon atoms, marketed by Gattefosse |
| ABIL 8851 B | dimethycone copolyol marketed by Goldschmidt |
| CARBOPOL 934, CARBOPOL 940 | carboxypolymethylenes marketed by Goldschmidt |
| TWEEN 60 | ethoxylated sorbitan monostearate |
| TWEEN 20 | ethoxylated sorbitan laurate |
| EDTA | ethylenediaminotetraacetic acid |
| UVB FILTER | 2-ethylhexyl 4-methoxycinnamate (trademark PARSOL MCX) |

EXAMPLE 1

Preparation to be reconstituted before use

| | | |
| --- | --- | --- |
| A) | Solvent | |
| | Carboxymethylcellulose | 0.30 g |
| | Preservatives in propylene glycol | 5.00 g |
| | Phenoxyethanol | 0.5 g |
| | Methyl 4-hydroxybenzoate | 0.1 g |
| | Ethyl 4-hydroxybenzoate | 0.1 g |
| | Propyl 4-hydroxybenzoate | 0.1 g |
| | Butyl 4-hydroxybenzoate | 0.1 g |
| | Propylene glycol | 4.1 g |
| | Ethoxylated hydrogenated castor oil | 1.00 g |
| | Fragrance | 0.20 g |
| | Demineralized water q.s. to | 100.00 g |
| B) | Powder | |
| | Betaine | 0.10 g |
| | Magnesium chloride | 0.05 g |
| | Potassium chloride | 0.10 g |
| | REVITALINE | 0.50 g |
| | Lactose q.s. to | 100.00 g |

EXAMPLE 2

Protective day cream

| | |
| --- | --- |
| Betaine | 0.05 g |
| Magnesium chloride | 0.05 g |
| Potassium chloride | 0.10 g |
| REVITALINE | 0.50 g |
| TWEEN 60 | 2.60 g |
| Silicon oil | 1.00 g |
| Cetyl alcohol | 2.00 g |
| Mineral oil | 3.00 g |
| Lanolin alcohol | 1.00 g |
| Perhydrosqualene | 1.00 g |
| Sorbitan monostearate | 2.40 g |
| Cetyl palmitate | 3.00 g |
| Isopropyl palmitate | 4.00 g |
| UVB FILTER | 2.00 g |
| Tetrasodium EDTA | 0.10 g |
| CARBOPOL 934 | 0.30 g |
| Triethanolamine | 0.30 g |
| Butylhydroxytoluene | 0.01 g |
| Preservatives in butylene glycol | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Fragrance | 0.30 g |
| Demineralized water q.s. to | 100.00 g |

EXAMPLE 3

Microemulsion

| | |
|---|---|
| Betaine | 0.10 g |
| Magnesium chloride | 0.05 g |
| Potassium pyroglutamate | 0.10 g |
| REVITALINE | 0.50 g |
| TWEEN 60 | 20.00 g |
| Glycerol | 28.00 g |
| Propylene glycol dipelargonate | 40.00 g |
| Ethyl 4-hydroxybenzoate | 0.30 g |
| Fragrance | 0.30 g |
| Demineralized water q.s. to | 100.00 g |

The microemulsion is obtained by mixing all the ingredients together and stirring until a clear solution is obtained.

EXAMPLE 4

Microemulsion

| | |
|---|---|
| Betaine | 0.20 g |
| Magnesium gluconate | 0.50 g |
| Potassium gluconate | 0.50 g |
| OXYDERMINE | 0.50 g |
| SOLUTOL HS 15 | 1.00 g |
| LABRAFAC HYDROPHYLE | 0.25 g |
| CETIOL HE | 0.20 g |
| ABIL 8851 B | 0.05 g |
| Propylene glycol | 12.50 g |
| Ethanol | 12.50 g |
| Carboxypolyvinyl polymer | 0.40 g |
| Fragrance | 0.30 g |
| Preservatives | 0.30 g |
| Colorant | q.s. |
| Demineralized water q.s. to | 100.00 g |
| Triethanolamine q.s. to | pH = 6 |

The microemulsion is prepared as described in Example 3.

EXAMPLE 5

Fluid make-up foundation

| | |
|---|---|
| Betaine | 0.10 g |
| Magnesium gluconate | 0.90 g |
| Potassium gluconate | 0.60 g |
| REVITALINE | 0.50 g |
| Ethoxylated soja sterols | 4.00 g |
| Soja sterols | 0.50 g |
| Glycerol monostearate | 1.00 g |
| Vegetable oil | 1.50 g |
| 2-Ethylhexyl palmitate | 4.00 g |
| Cetyl alcohol | 0.50 g |
| Capric/caprylic triglycerides | 1.50 g |
| Silicon oil | 1.00 g |
| Mineral oil | 1.80 g |
| Lanolin alcohols | 0.20 g |
| Propylene glycol dipelargonate | 3.00 g |
| Lecithin | 1.00 g |
| Preservatives in butylene glycol | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| CARBOPOL 940 | 0.20 g |
| Triethanolamine | 0.20 g |
| Tetrasodium EDTA | 0.10 g |
| Butylhydroxytoluene | 0.01 g |
| Fragrance | 0.30 g |

EXAMPLE 6

Night cream

| | |
|---|---|
| Betaine | 0.05 g |
| Magnesium gluconate | 0.90 g |
| Potassium pyroglutamate | 0.60 g |
| REVITALINE | 0.50 g |
| Cetyl alcohol | 2.00 g |
| Stearin | 2.50 g |
| Glycerol monostearate | 5.00 g |
| Isopropyl palmitate | 5.00 g |
| Vegetable oil | 3.00 g |
| Mineral oil | 2.00 g |
| Perhydosqualene | 2.00 g |
| Silicon oil | 1.00 g |
| Shea butter | 2.00 g |
| Preservatives in butylene glycol | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| Triethanolamine | 5.50 g |
| Tetrasodium EDTA | 0.10 g |
| Fragrance | 0.30 g |
| Water q.s. to | 100.00 g |

EXAMPLE 7

Gel

| | |
|---|---|
| Betaine | 0.10 g |
| Magnesium gluconate | 0.90 g |
| Potassium gluconate | 0.60 g |
| REVITALINE | 0.50 g |
| CARBOPOL 940 | 0.20 g |
| Polyethylene glycol | 3.00 g |
| Preservatives in butylene glycol | 5.00 g |
| Phenoxyethanol | 0.5 g |
| Methyl 4-hydroxybenzoate | 0.1 g |
| Ethyl 4-hydroxybenzoate | 0.1 g |
| Propyl 4-hydroxybenzoate | 0.1 g |
| Butyl 4-hydroxybenzoate | 0.1 g |
| Butylene glycol | 4.1 g |
| TWEEN 20 | 0.50 g |
| Triethanolamine | 0.25 g |
| Fragrance | 0.20 g |
| Demineralized water q.s. to | 100.00 g |

EXAMPLE 8

Serum

| | |
|---|---|
| Betaine | 0.10 g |
| Magnesium gluconate | 0.90 g |
| Potassium gluconate | 0.60 g |
| Yeast extract (VITACELL LS 1917) | 0.50 g |
| Hydroxypropylmethylcellulose | 0.30 g |
| Propylene glycol | 5.00 g |
| Glycerin | 5.00 g |
| Ethoxylated oleic alcohol | 0.50 g |
| Fragrance | 0.30 g |
| Tetrasodium EDTA | 0.10 g |
| Preservatives | 0.50 g |
| Bovine albumin | 5.00 g |
| Demineralized water q.s. to | 100.00 g |

EXAMPLE 9

Make-up foundation

| | |
|---|---|
| Betaine | 0.10 g |
| Magnesium gluconate | 0.90 g |
| Potassium pyroglutamate | 0.60 g |
| Yeast extract (VITACELL LS 1917) | 0.50 g |
| Tetrasodium EDTA | 0.10 g |

-continued

| | |
|---|---|
| Carboxymethylcellulose | 0.20 g |
| Aluminum magnesium silicate | 1.00 g |
| Ethoxylated sorbitan laurate | 1.00 g |
| Propylene glycol | 5.00 g |
| Titanium oxide | 2.00 g |
| Talc | 1.00 g |
| Pigments | 1.00 g |
| Triethanolamine | 0.50 g |
| Preservatives | 0.50 g |
| Cetyl alcohol | 1.00 g |
| Lanolin alcohol | 3.00 g |
| Stearic acid | 1.80 g |
| Propylene glycol monostearate | 3.00 g |
| Isopropyl palmitate | 8.00 g |
| Vegetable oil | 2.00 g |
| Antioxidants | 0.05 g |
| Fragrance | 0.30 g |
| Demineralized water q.s. to | 100.00 g |

We claim:

1. A cosmetic composition which comprises a mixture of
   (a) betaine $((CH_3)_3N^+CH_2COO^-)$ or hydrated betaine or an addition salt or hydrated addition salt thereof with a dermocompatible acid,
   (b) ATP or an ATP generating system,
   (c) a magnesium salt, and
   (d) a potassium salt,
   in a cosmetically acceptable vehicle for topical administration, said mixture being contained in said composition in an amount effective to improve the appearance of ageing skin.

2. The composition of claim 1 which comprises
   (a) from 0.001 to 1% of betaine $((CH_3)_3N^+CH_2COO^-)$ or an addition salt or hydrated addition salt thereof with a dermocompatible acid,
   (b) from 0.045 to 4.5% of ATP or an ATP generating system,
   (c) from 10 ppb to 0.3% of $Mg^{++}$, and
   (d) from 0.0001 to 0.6% of $K^+$,
   the above percentages being by weight.

3. The composition of claim 2 which comprises
   (a) from 0.03 to 0.3% of betaine $((CH_3)_3N^+CH_2COO^-)$ or an addition salt or hydrated addition salt thereof with a dermocompatible acid,
   (b) from 0.15 to 1.5% of ATP or an ATP generating system,
   (c) from 15 ppb to 0.1% of $Mg^{++}$, and
   (d) from 0.001 to 0.2% of $K^+$,
   the above percentages being by weight.

4. The composition of claim 3 which comprises
   (a) from 0.05 to 0.25% of betaine $((CH_3)_3N^+CH_2COO^-)$ or an addition salt or hydrated addition salt thereof with a dermocompatible acid,
   (b) from 0.25 to 1% of ATP or an ATP generating system,
   (c) from 20 ppb to 0.06% of $Mg^{++}$, and
   (d) from 0.002 to 0.1% of $K^+$,
   the above percentages being by weight.

5. The composition of claim 1, wherein the ATP generating system is an extract derived from eucaryotic cells.

6. The composition of claim 5, wherein the ATP generating system is an extract derived from yeast cells or bovine spleen cells.

7. The composition of claim 5, wherein the ATP generating system is selected from the group consisting of
   (a) a purified yeast cell extract marketed under the tradename VITACELL LS 1917, comprising amino acids and yeast cellular proteins.
   (b) a purified bovine spleen extract marketed under the tradename OXYDERMINE, comprising spleen cell proteins, fats and carbohydrates, and
   (c) a purified bovine spleen extract marketed under the tradename REVITALINE, comprising spleen cell proteins and nutrients.

8. The composition of claim 1 wherein the magnesium and potassium salts are selected from the group consisting of the corresponding chlorides, gluconates and pyroglutamates.

9. A cosmetic composition as claimed in claim 1, consisting essentially of the recited ingredients.

10. A method of treating the skin of a living human to improve the appearance of ageing skin, which comprises applying to the skin a cosmetic preparation comprising a mixture of
    (a) betaine $((CH_3)_3N^+CH_2COO^-)$ or hydrated betaine or an addition salt or hydrated addition salt thereof with a dermocompatible acid,
    (b) ATP or an ATP generating system,
    (c) a magnesium salt, and
    (d) a potassium salt,
    in a cosmetically acceptable vehicle for topical administration, said mixture being contained in said cosmetic preparation in an amount effective to improve the appearance of ageing skin.

11. A method according to claim 10, wherein said ATP generating system is an extract derived from yeast cells or bovine spleen cells.

12. A method according to claim 10, wherein said mixture is comprised of
    (a) from 0.0001 to 1% of betaine $((CH_3)_3N^+CH_2COO)$ or an addition salt or hydrated addition salt thereof with a dermocompatible acid,
    (b) from 0.045 to 4.5% of ATP or an ATP generating system,
    (c) from 10 ppb to 0.3% of $Mg^{++}$, and
    (d) from 0.0001 to 0.6% of $K^+$,
    the above percentages being by weight.

13. A method according to claim 10, wherein said mixture is comprised of
    (a) from 0.03 to 0.3% of betaine $((CH_3)_3N^+CH_2COO^-)$ or an addition salt or hydrated addition salt thereof with a dermocompatible acid,
    (b) from 0.15 to 1.5% of ATP or an ATP generating system,
    (c) from 15 ppb to 0.1% of $Mg^{++}$, and
    (d) from 0.001 to 0.2% of $K^+$,
    the above percentages being by weight.

14. A method according to claim 10, wherein said mixture is comprised of
    (a) from 0.05 to 0.25% of betaine $((CH_3)_3N^+CH_2COO^-)$ or an addition salt or hydrated addition salt thereof with a dermocompatible acid,
    (b) from 0.25 to 1.0% of ATP or an ATP generating system,
    (c) from 20 ppb to 0.06% of $Mg^{++}$, and
    (d) from 0.002 to 0.1% of $K^+$,
    the above percentages being by weight.

15. A method according to claim 10, wherein said ATP generating system is selected from the group consisting of (a) a purified yeast cell extract marketed under the tradename VITACELL LS 1917, comprising amino acids and yeast cellular proteins, (b) a purified bovine spleen extract marketed under the tradename OXYDERMINE, comprising spleen cell proteins, fats and carbohydrates, and (c) a purified bovine spleen extract marketed under the tradename REVITALINE, comprising spleen cell proteins and nutrients.

16. A method according to claim 10, wherein said magnesium and potassium salts are selected from the group consisting of the corresponding chlorides, gluconates and pyroglutamates.

* * * * *